United States Patent [19]

Sertich

[11] 4,427,384
[45] Jan. 24, 1984

[54] VIBRATORY DENTAL SCALER

[76] Inventor: Anthony T. Sertich, 137 MacIntyre La., Allendale, N.J. 07401

[21] Appl. No.: 400,921

[22] Filed: Jul. 22, 1982

[51] Int. Cl.³ .......................... A61C 1/07; A61C 3/03
[52] U.S. Cl. .................................... 433/120; 366/124
[58] Field of Search ........................ 433/120; 366/124

[56] References Cited

U.S. PATENT DOCUMENTS 3,229,961  1/1966  Bodine .............................. 366/124
3,822,054  7/1974  Matson .............................. 366/124

Primary Examiner—Robert Peshock
Attorney, Agent, or Firm—Samuelson & Jacob

[57] ABSTRACT

A dental scaler in which a scaling tool is coupled to a relatively rigid inner tubular member supported within an outer housing for vibration in response to relatively high speed rotation of a thin-walled tubular element located within an inner chamber in the inner tubular member and rotated by the passage of air, under pressure, through the inner chamber.

22 Claims, 5 Drawing Figures

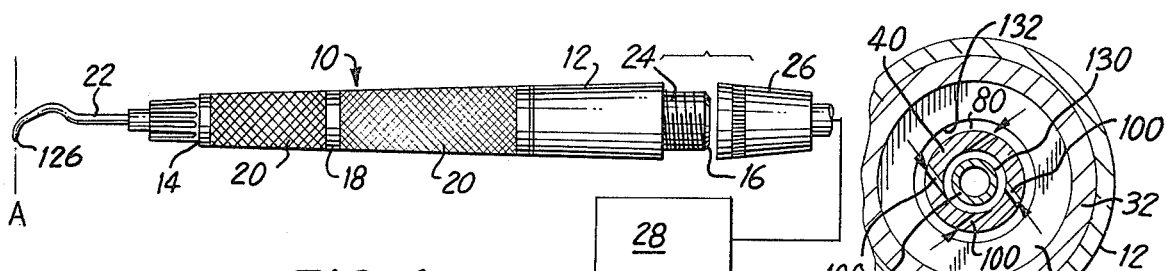
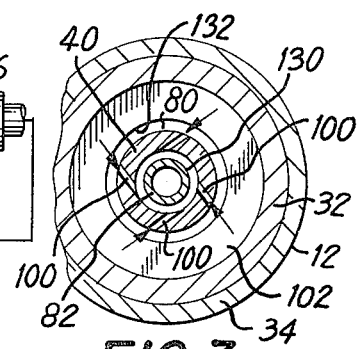
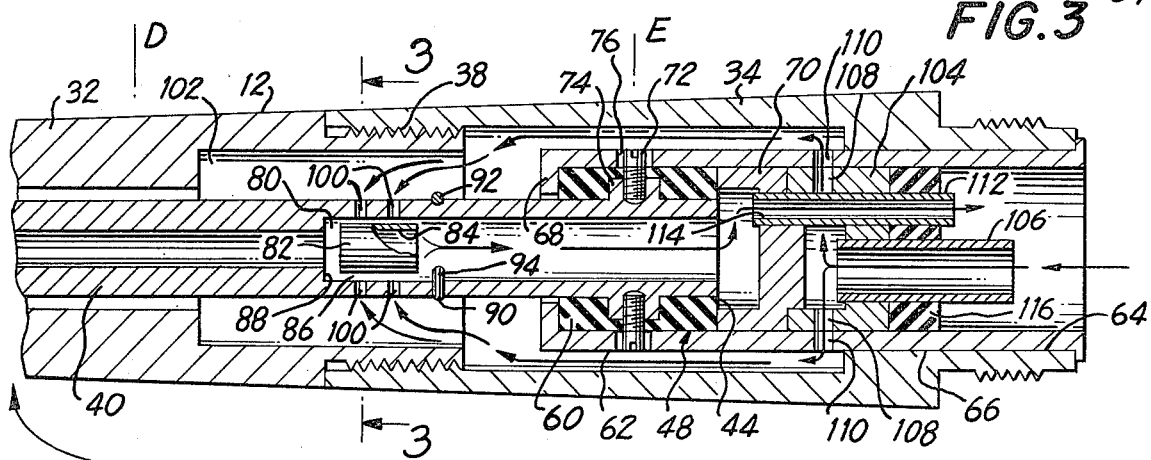
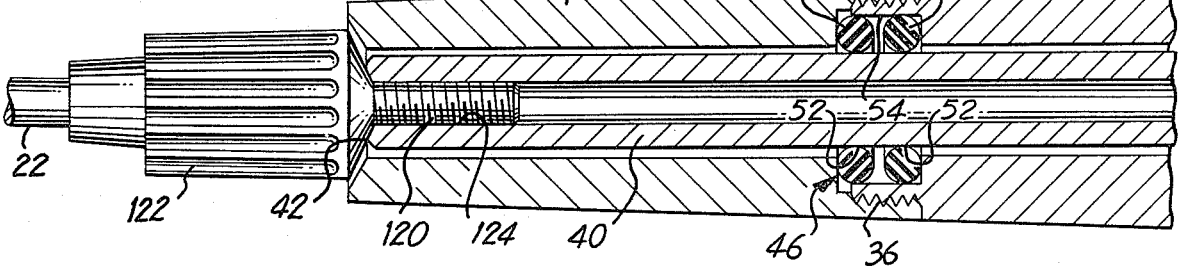
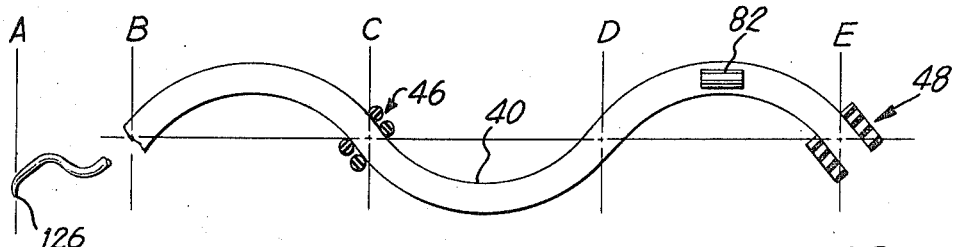
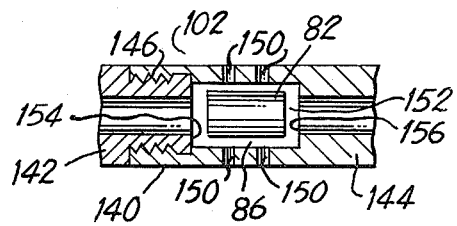

VIBRATORY DENTAL SCALER

The present invention relates generally to dental scalers and pertains, more specifically, to an air-driven vibratory dental scaler which incorporates an improved mechanism for producing vibrations to be transmitted to the scaling tool of the dental scaler.

In may earlier patent, U.S. Pat. No. Re. 29,687, I disclosed an air-driven dental scaler which provides several advantages over previously available dental scalers. In particular, that dental scaler has relatively few moving parts, is mechanically uncomplicated and provides efficient transfer of vibrational energy to a dental scaling tool, while relatively little vibration is transferred to the handle of the instrument. A later patent, U.S. Pat. No. 4,260,380 to Nash, discusses in more detail the relative advantages of my earlier air-driven dental scaler as compared to other types, such as those illustrated in U.S. Pat. Nos. 3,082,529 and 3,444,622 to Mills et al, U.S. Pat. No. 3,526,962 to Fuerst and U.S. Pat. No. 3,703,037 to Robinson.

The dental scaler of the present invention is an improvement over my earlier dental scaler in that it meets several objectives and provides several advantages, as follows:

It is an object of the present invention to provide an air-driven vibratory dental scaler which is capable of operating at frequencies generally higher than those attained by my earlier dental scaler.

Another object of the invention is to provide an air-driven dental scaler which operates at lower noise levels than my earlier dental scaler.

Still another object of the invention is to provide an air-driven dental scaler which is more compact than my earlier dental scaler, while maintaining a simple design and construction.

Yet another object of the invention is to provide an air-driven dental scaler which is more efficient in use and is more comfortable from the standpoint of both the dental operator and the patient.

A further object of the invention is to provide a vibratory mechanism for use in various other implements for enabling operation at higher frequencies, with lower noise levels, than heretofore attained in devices of the type disclosed herein.

A still further object of the invention is to provide a vibratory mechanism for use in various small implements for enabling the construction of a more compact implement.

Yet a further object of the invention is to provide a vibratory mechanism for use in a variety of implements and instruments for enabling a simplified and economical construction.

The above objects, as well as still further objects and advantages, are attained by the present invention which may be described briefly as an improvement in a vibratory device, such as a dental scaler of the type having a scaling tool to be vibrated at high frequency, the improvement including the combination comprising an outer tubular housing extending longitudinally between opposite ends; a relatively rigid inner tubular member extending longitudinally within the housing between a first end a second end; support means for supporting the inner tubular member within the outer tubular housing; an outer chamber located between the outer tubular housing and the inner tubular member; an inner chamber located within the inner tubular member and having an inner periphery; a relatively thin-walled tubular element having an outer periphery and located at a predetermined longitudinal position within the inner chamber; at least one inlet port, and preferably a plurality of inlet ports, in the inner tubular member and extending from the outer chamber to the inner chamber at the predetermined longitudinal position; and an outlet port communicating with the inner chamber; the relative dimensions of the inner periphery of the inner chamber and the outer periphery of the tubular element providing a prescribed clearance between the tubular element and the inner tubular member for enabling relatively high speed rotation of the tubular element within the inner chamber in response to the passage of fluid under pressure from the outer chamber through the inner chamber, by means of the inlet and outlet ports, and the concommitant transmission of high-frequency vibratory energy from the rotating tubular element to the inner tubular member.

The invention will be understood more fully, while still further objects and advantages will become apparent, in the following detailed description of preferred embodiments illustrated in the accompanying drawing, in which:

FIG. 1 is an elevational view of a dental scaler constructed in accordance with the invention, together with a schematic representation of a work station where the instrument is to be used;

FIG. 2 is an enlarged longitudinal cross-sectional view of the dental scaler;

FIG. 3 is a transverse cross-sectional view taken along line 3—3 of FIG. 2;

FIG. 4 is a diagram showing a typical standing wave pattern, exaggerated for illustrative purposes, indicating the location of various operating components of the dental scaler relative to the wave pattern generated during operation of the dental scaler; and FIG. 5 is a fragmentary longitudinal cross-sectional view showing an alternate construction.

Referring now to the drawing, and especially to FIG. 1 thereof, a dental scaler constructed in accordance with the invention is shown at 10 and is seen to include an outer housing 12 extending longitudinally between a forward end 14 and a rearward end 16. Outer surface 18 of the housing 12 is knurled along portion 20 to provide finger grips by which a dental operator may grasp the implement during use. A typical scaling tool 22 is shown at the forward end 14, while a threaded nipple 24 is provided at the rearward end 16 to receive a threaded coupling 26, enabling the dental scaler 10 to be coupled to a supply 28 of air under pressure usually available at the point of use of the implement.

Turning now to FIG. 2, housing 12 is seen to be constructed in the form of a segmented outer tubular member including a forward tubular segment 30, an intermediate tubular segment 32 and a rearward tubular segment 34. A forward threaded coupling 36 joins segment 30 to segment 32 and a rearward threaded coupling 38 joins segment 32 to segment 34. An inner tubular member shown in the form of shaft 40 extends longitudinally within housing 12 between a first end 42 and a second end 44 and is suspended within the housing 12 by support means shown in the form of forward support 46 and rearward support 48. Both of the supports 46 and 48 provide a resilient suspension arrangement, for purposes which will be discussed in further detail below.

Forward support 46 includes a pair of elastomeric rings 50 which grip shaft 40 and 52, adjacent first end 42, and are seated within a recess 54 in housing 12, accessible by virtue of forward threaded coupling 36. Rearward support 48 includes an elastomeric collar 60 fitted upon shaft 40 adjacent second end 44 and seated within a sleeve 62 secured within rearward tubular segment 34 of housing 12, as by an interference fit along complementary surfaces 64 and 66. Collar 60 is secured against longitudinal movement relative to sleeve 62 by a lip 68, integral with sleeve 62 and extending radially inwardly at one end of the sleeve, and by a retainer 70 fitted into the sleeve and secured against the collar 60. A pair of pins 72 are threaded into a raised rib 74 on shaft 40 and project through corresponding apertures 76 in sleeve 62. Clearance is provided between pins 72 and apertures 76 to allow for limited movement of the shaft 40 relative to sleeve 62, as will be described in greater detail below.

Shaft 40 includes a longitudinally extending inner chamber 80 within which there is located a tubular element shown in the form of a rotor 82 having a relatively thin cylindrical wall 84 (also see FIG. 3). Rotor 82 is confined to a predetermined longitudinal position 86 by stop means in the form of a laterally-extending shoulder 88 in shaft 40 and a spring clip retainer 90 which is seated in a complementary groove 92 in shaft 40 and includes a leg 94 projecting radially into the inner chamber 80 to confine the rotor 82 to the portion of the inner chamber 80 bounded by shoulder 88 and leg 94.

A plurality of inlet ports 100 extend through the wall of shaft 40 at position 86, are arrayed around the perimeter of shaft 40, and interconnect the inner chamber 80 with a longitudinally extending, generally annular outer chamber 102 established within housing 12 between the housing and shaft 40 and coaxial with inner chamber 80. A fitting 104 is secured within sleeve 62 and carries an inlet tube 106 which communicates with outer chamber 102 through passages 108 in the fitting 104 and passages 110 in the sleeve 62. Similarly, an outlet tube 112 is carried by fitting 104 and passes through retainer 70 to provide an outlet port 114 which communicates with the inner chamber 80. A seal 116 is seated against the fitting 104 such that complementary threaded coupling 26, available at the work station where dental scaler 10 is to be used, can be attached to the threaded nipple 24 to couple source 28 of air under pressure to inlet tube 106 and to connect an exhaust to outlet tube 112.

Air under pressure supplied to inlet tube 106 will enter outer chamber 102, which essentially surrounds the inner chamber 80, and will pass into inner chamber 80 through inlet ports 100, as indicated by the arrows in FIG. 2, and then will pass out of the inner chamber 80 through port 114. It is noted here that the elastomeric rings 50 of forward support 46 serves to seal the forwardmost end of inner chamber 80 against the leakage of air from inner chamber 80. Inlet ports 100 direct the air to rotor 82 which then rotates at high speed within the inner chamber 80 and transmits vibratory energy to shaft 40. Scaling tool 22 is coupled to shaft 40 by means of a threaded stud 120 which projects from a fluted collar 122 of scaling tool 22 and engages a complementary thread 124 in shaft 40 such that the tip 126 (see FIG. 1) of scaling tool 22 will vibrate to accomplish the desired scaling operation. A suitable scaling tool is disclosed in my earlier patent, U.S. Pat. No. 4,283,174.

Referring now to FIG. 3, inlet ports 100 extend through the wall of shaft 40 at an angle to the radial direction so that the air which passes through inlet ports 100 is directed generally tangential to the outer periphery 130 of the rotor 82, as indicated by the arrows in FIG. 3. The clearance provided between the inner periphery 132 of the inner chamber 80 and the outer periphery 130 of the rotor 82 enables high-speed rotation of the rotor 82 in response to the passage of air through inlet ports 100 and over the outer periphery 130 of the rotor. A thin film of air within that clearance provides a fluid bearing within which the rotor 82 will rotate at high speed, as well as enabling cooling of the rotor 82 and the shaft 40 during such high speed operation. The thin-walled structure of rotor 82 not only provides relatively light weight for enabling effective high-speed rotation, but renders the cylindrical wall 84 of rotor 82 elastically deformable in radial directions so that vibratory energy is generated by the rotor through a combination of rotation and periodic elastic deformation in radial directions as the rotor rotates at high speed. Thus, whereas in my earlier device, described in the aforesaid U.S. Pat. No. Re. 29,687, a thin-walled rotor is supported upon a relatively rigid shaft for high speed rotation around the outer periphery of the shaft, and the shaft tends to reinforce the cylindrical configuration of the rotor, in the present construction, rotor 82 is not supported internally and the thin-walled construction, which might have been thought to be susceptible to collapse under the stress of operation, instead provides the unexpected advantage of enhanced periodic radial elastic deformation for the generation of vibratory energy. Even though some periodic radial elastic deformation is present during the rotation of the rotor of my earlier device, the forces created by the pressure of the fluid and by such rotation of the rotor are cumulative and may tend to burst the rotor; however, in the present arrangement the rotor 82 is contained within chamber 80 and the forces created by the pressure of the fluid and by rotation of the rotor 82 are opposed, thereby tending to reduce the possibility of bursting.

In a typical dental scaler constructed in accordance with the present invention, the wall thickness of the shaft 40 at longitudinal position 86 is about 1/32 inch, rendering the shaft 40 relatively rigid. The thickness of wall 84 of rotor 82 is about 0.003 to 0.004 inch, while the clearance between outer periphery 130 and inner periphery 132 is about 0.004 to 0.005 inch. Shaft 40 preferably is constructed of brass, and the preferred material for rotor 82 is stainless steel, although other suitable materials will be apparent to those skilled in the art of materials. Operating with a source 28 of air under a pressure of about 40 to 45 psi, which ordinarily is available at conventional dental work stations, the frequency of vibration of the scaling tool 22 is about 9000 hz., as opposed to the usual operating frequency of about 6000 hz. in my earlier dental scaler.

The mode of vibration of shaft 40 is illustrated diagrammatically in FIG. 4. The shaft 40 is shown in an exaggerated depiction of a wave-pattern followed by the shaft. The working tip 126 of scaling tool 22 is located at a point A of maximum amplitude, while the coupling means which couples the scaling tool 22 to shaft 40 is located at a node B. The forward support 46 is located at a node C and the resilient nature of the support 46 enables the appropriate vibration of shaft 40. Likewise, rearward support 48 is located at a node E, at least one full wave-length from node C, with the resilient suspension provided by rearward support 48 enabling the desired vibration of shaft 40. It is here noted that the clearance provided between pins 72 and apertures 76, as described above in connection with FIG. 2, allow for sufficient resilient movement so that vibration of shaft 40 is not impeded. The rotor 82 is located at predetermined longitudinal position 86 which preferably is one quarter wave-length forward of rearward support 48, at a position of maximum amplitude, and a node D is located at the mid-point between the forward support 46 and the rearward support 48.

Turning now to FIG. 5, an alternate construction is illustrated in which the structure of the inner tubular member, here shown as shaft 140, is modified at the prescribed longitudinal position 86 of rotor 82. In this instance, shaft 140 is constructed of a forward section 142 and a rearward section 144, joined together by a threaded connection at 146. Forward section 142 is supported by a forward support identical to forward support 46 while rearward section 144 is supported by a rearward support identical to rearward support 48. As in the embodiment of FIGS. 1 through 3, rotor 82 is driven by fluid passed through inlet ports 150 which interconnect outer chamber 102 with an inner chamber 152. In the present embodiment, however, rotor 82 is confined longitudinally, or axially, to location 86 by stop means in the form of a forward shoulder 154 on forward section 142 of shaft 140 and a rearward shoulder 156 on rearward section 144 of shaft 140, both of which shoulders extent laterally into the inner chamber 152, thus eliminating the need for spring clip retainer 90.

The overall construction illustrated and described above in connection with both embodiments is more compact than that attained in my earlier device, by virtue of the location of the rotor 82 inside the shaft 40, or 140, rather than outside. The internal location of rotor 82 reduces the noise level considerably during operation of the dental scaler, rendering the instrument more comfortable for both the dental operator and the patient. In addition, air flow within the instrument is generally in axial directions throughout the coaxially related inner and outer chambers 80 and 102 or 152, thereby increasing the efficiency of the instrument while further reducing noise. Furthermore, placing the rotor 82 inside the shaft 40, rather than outside, enables the use of a smaller diameter, higher speed rotor in connection with a relatively rigid shaft 40 of approximately the same dimensions as in my earlier device, thereby attaining higher frequency vibratory energy.

Although the present invention has been described with specific reference to a dental scaler, it also is applicable to vibratory devices or like or similar configurations which are used for other purposes, such as medical and veterinary uses, as well as in general industrial cleaning, polishing, deburring and like applications.

It is to be understood that the above detailed descriptions of embodiments of the invention are provided by way of example only. Various details of design and construction may be modified without departing from the true spirit and scope of the invention as set forth in the appended claims.

The embodiments of the invention in which an exclusive property or privilege is claimed are defined as follows:

1. A dental scaler of the type having a scaling tool to be vibrated at a high frequency, the dental scaler comprising:
   an outer tubular housing extending longitudinally between opposite ends;
   a relatively rigid inner tubular member extending longitudinally within the housing between a first end and a second end;
   coupling means for coupling the scaling tool to the first end of the inner tubular member;
   support means for supporting the inner tubular member within the outer tubular housing;
   an outer chamber located between the outer tubular housing and the inner tubular member;
   an inner chamber located within the inner tubular member and having an inner periphery;
   a relatively thin-walled tubular element having an outer periphery and located at a predetermined longitudinal position within the inner chamber;
   at least one inlet port in the inner tubular member and extending from the outer chamber to the inner chamber at the predetermined longitudinal position; and
   an outlet port communicating with the inner chamber;
   the relative dimensions of the inner periphery of the inner chamber and the outer periphery of the tubular element providing a prescribed clearance between the tubular element and the inner tubular member for enabling relatively high speed rotation of the tubular element within the inner chamber in response to the passage of fluid under pressure from the outer chamber through the inner chamber, by means of the inlet and outlet ports, and the concommitant transmission of high-frequency vibratory energy from the rotating tubular element to the inner tubular member for vibration of the scaling tool.

2. The invention of claim 1 wherein the support means includes a resilient forward support adjacent the first end of the inner tubular member, and a resilient rearward support adjacent the second end of the inner tubular member.

3. The invention of claim 2 wherein the predetermined longitudinal position is located between the forward support and the rearward support.

4. The invention of claim 1 or 3 including stop means extending laterally into the inner chamber for confining the tubular element longitudinally to the predetermined longitudinal position.

5. The invention of claim 1 wherein the inner periphery of the inner chamber is cylindrical, at least at the predetermined longitudinal position, and the outer periphery of the tubular element is cylindrical.

6. The invention of claim 5 wherein the prescribed clearance between the outer periphery of the tubular element and the inner periphery of the inner chamber is such that a fluid bearing will be established therein upon said passage of fluid under pressure to enable rotation of the tubular element in said fluid bearing.

7. The invention of claim 1, 5 or 6 including a plurality of inlet ports in the inner tubular member, the inlet ports being arrayed around the perimeter of the inner tubular member.

8. The invention of claim 7 wherein the inlet ports extend along directions which direct said fluid generally tangential to the outer periphery of the tubular element.

9. The invention of claim 1 wherein the inner chamber extends longitudinally within the inner tubular member and the outer chamber extends longitudinally within the outer tubular housing and generally coaxial with the inner chamber.

10. The invention of claim 9 wherein the outer chamber is generally annular and surrounds the inner chamber at the predetermined longitudinal position.

11. The invention of claim 1, 5, 6, 9 or 10 wherein the tubular element includes an elastically deformable wall such that high frequency vibratory energy will be generated by periodic elastic deformation of the wall of the tubular element during rotation thereof in reponse to said passage of fluid under pressure from the outer chamber through the inner chamber.

12. In a vibratory device, the combination comprising:
   an outer housing;
   a relatively rigid inner tubular member extending longitudinally within the housing between a first end and a second end;
   support means for supporting the inner tubular member within the outer housing;
   an outer chamber located between the outer housing and the inner tubular member;
   an inner chamber located within the inner tubular member and having an inner periphery;
   a relatively thin-walled tubular element having an outer periphery and located at a predetermined longitudinal position within the inner chamber;
   at least one inlet port in the inner tubular member and extending from the outer chamber to the inner chamber at the predetermined longitudinal position; and
   an outlet port communicating with the inner chamber;
   the relative dimensions of the inner periphery of the inner chamber and the outer periphery of the tubular element providing a prescribed clearance between the tubular element and the inner tubular member for enabling relatively high speed rotation of the tubular element within the inner chamber in response to the passage of fluid under pressure from the outer chamber through the inner chamber, by means of the inlet and outlet ports, and the concomitant transmission of high-frequency vibratory energy from the rotating tubular element to the inner tubular member.

13. The invention of claim 12 wherein the support means includes a resilient forward support adjacent the first end of the inner tubular member, and a resilient rearward support adjacent the second end of the inner tubular member.

14. The invention of claim 13 wherein the predetermined longitudinal position is located between the forward support and the rearward support.

15. The invention of claim 12 or 13 including stop means extending laterally into the inner chamber for confining the tubular element longitudinally to the predetermined longitudinal position.

16. The invention of claim 12 wherein the inner periphery of the inner chamber is cylindrical, at least at the predetermined longitudinal position, and the outer periphery of the tubular element is cylindrical.

17. The invention of claim 16 wherein the prescribed clearance between the outer periphery of the tubular element and the inner periphery of the inner chamber is such that a fluid bearing will be established therein upon said passage of fluid under pressure to enable rotation of the tubular element in said fluid bearing.

18. The invention of claim 12, 16 or 17 including a plurality of inlet ports in the inner tubular member, the inlet ports being arrayed around the perimeter of the inner tubular member.

19. The invention of claim 18 wherein the inlet ports extend along directions which direct said fluid generally tangential to the outer periphery of the tubular element.

20. The invention of claim 12 wherein the inner chamber extends longitudinally within the inner tubular member and the outer chamber extends longitudinally within the outer housing and generally coaxial with the inner chamber.

21. The invention of claim 20 wherein the outer chamber is generally annular and surrounds the inner chamber at the predetermined longitudinal position.

22. The invention of claim 12, 16, 17, 20 or 21 wherein the tubular element includes an elastically deformable wall such that high frequency vibratory energy will be generated by periodic elastic deformation of the wall of the tubular element during rotation thereof in response to said passage of fluid under pressure from the outer chamber through the inner chamber.

* * * * *